(12) United States Patent
Haddock et al.

(10) Patent No.: US 7,842,038 B2
(45) Date of Patent: *Nov. 30, 2010

(54) METHOD FOR USING RETRACTABLE STYLET AND CANNULA COMBINATION TO FORM AN OPENING IN BONE

(75) Inventors: Sean M. Haddock, Memphis, TN (US); Jeff J. Justis, Germantown, TN (US); T. Andrew Simonton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 576 days.

This patent is subject to a terminal disclaimer.

(21) Appl. No.: 11/417,633

(22) Filed: May 4, 2006

(65) Prior Publication Data
US 2007/0260255 A1 Nov. 8, 2007

(51) Int. Cl.
*A61B 17/00* (2006.01)
(52) U.S. Cl. .................................. 606/79; 604/164.01
(58) Field of Classification Search ............... 606/79; 482/108; 604/164.01; 175/77, 80, 246, 255
See application file for complete search history.

(56) References Cited

U.S. PATENT DOCUMENTS

| | | | | |
|---|---|---|---|---|
| 3,289,290 A * | 12/1966 | Sandor | ...................... | 29/432 |
| 4,012,984 A * | 3/1977 | Matuschek | ................... | 411/34 |
| 4,498,902 A * | 2/1985 | Ash et al. | ............. | 604/164.05 |
| 4,793,363 A * | 12/1988 | Ausherman et al. | ......... | 600/567 |
| 4,838,282 A | 6/1989 | Strasser et al. | | |
| 5,125,144 A * | 6/1992 | Clark | ...................... | 29/240 |
| 5,158,543 A * | 10/1992 | Lazarus | ................... | 604/164.1 |
| 5,257,632 A * | 11/1993 | Turkel et al. | ................ | 600/567 |
| 5,295,974 A * | 3/1994 | O'Laughlin | ................. | 604/198 |
| 5,385,151 A | 1/1995 | Scarfone et al. | | |
| 5,472,426 A * | 12/1995 | Bonati et al. | ............. | 604/164.1 |
| 5,634,473 A * | 6/1997 | Goldenberg et al. | ........ | 600/567 |
| 5,762,629 A * | 6/1998 | Kambin | ................. | 604/164.11 |
| 5,772,661 A | 6/1998 | Michelson | | |
| 5,779,708 A * | 7/1998 | Wu | ............................. | 606/80 |
| 5,868,684 A * | 2/1999 | Ahlstroem et al. | .......... | 600/564 |
| 5,897,561 A * | 4/1999 | Raines | ....................... | 606/108 |
| 5,919,172 A * | 7/1999 | Golba, Jr. | .................... | 604/272 |
| 6,007,519 A * | 12/1999 | Rosselli | ................. | 604/164.01 |
| 6,033,411 A * | 3/2000 | Preissman | .................... | 606/99 |
| 6,080,155 A | 6/2000 | Michelson | | |
| 6,224,607 B1 | 5/2001 | Michelson | | |
| 6,261,022 B1 * | 7/2001 | Dalebout et al. | ............ | 482/107 |
| 6,325,812 B1 * | 12/2001 | Dubrul et al. | ............... | 606/185 |
| 6,461,330 B1 * | 10/2002 | Miyagi | ........................ | 604/117 |
| 6,520,907 B1 * | 2/2003 | Foley et al. | ................. | 600/114 |
| 6,554,778 B1 | 4/2003 | Fleming, III | | |
| 6,641,564 B1 * | 11/2003 | Kraus | ...................... | 604/164.1 |
| 6,733,506 B1 * | 5/2004 | McDevitt et al. | ............ | 606/104 |
| 7,081,122 B1 * | 7/2006 | Reiley et al. | ................. | 606/185 |
| 7,359,755 B2 * | 4/2008 | Jones et al. | .................. | 607/117 |
| 2002/0177897 A1 | 11/2002 | Michelson | | |
| 2002/0188300 A1 * | 12/2002 | Arramon et al. | ............. | 606/93 |
| 2003/0236506 A1 * | 12/2003 | Schofield et al. | ............ | 604/272 |

(Continued)

*Primary Examiner*—Thomas C Barrett
*Assistant Examiner*—David W Bates
(74) *Attorney, Agent, or Firm*—Martin & Ferraro, LLP (57) ABSTRACT

In one preferred aspect, a method is provided for forming an opening in bone for the sequential dilation of tissue.

17 Claims, 8 Drawing Sheets

U.S. PATENT DOCUMENTS

2007/0255281 A1* 11/2007 Simonton et al. ............. 606/60
2007/0255282 A1* 11/2007 Simonton et al. ............. 606/60
2007/0260184 A1* 11/2007 Justis et al. ............ 604/164.01

* cited by examiner

METHOD FOR USING RETRACTABLE STYLET AND CANNULA COMBINATION TO FORM AN OPENING IN BONE

BACKGROUND OF THE INVENTION

1. Field of the Invention

The present invention relates generally to a surgical instrument for insertion into human tissue and a method for use thereof.

2. Description of the Prior Art

Instruments and methods exist to penetrate and dilate tissue. One problem with conventional instruments is that when the instrument includes multiple components, it is often difficult to efficiently and reliably secure the components to one another. Another problem is that when multiple components have multiple handles, the disengagement of one component from another is more cumbersome, resulting in surgical inefficiency.

In surgical procedures involving sequential dilation of tissue, it is typical to use multiple instruments in succession to dilate the tissue to meet a desired surgical objective. For example, a guide wire is often inserted first, followed by a larger diameter stylet, which is then removed, followed by yet another instrument having a larger diameter to increase the diameter of the opening. Successive insertion and removal of multiple instruments is a time-consuming process that can hamper the surgical procedure. Additionally, the positioning of separate smaller instruments within larger instruments may lead to imprecise results as it is more difficult to maintain the instruments coaxial with one another, or limit the depth of insertion of the instruments relative to one another.

Accordingly, there exists a need for a surgical instrument having a configuration so that multiple components may be individually or in combination engaged to a handle for easier insertion and removal of the surgical instrument and its components from a patient. There also exists a need for a surgical instrument capable of performing sequential dilation without the need to successively insert and remove a multitude of individual instruments.

SUMMARY OF THE INVENTION

The present invention in one preferred embodiment includes a method for forming an opening in bone. The method includes providing a surgical instrument including an outer sleeve having a distal end, a proximal end, a passage therethrough, and a mid-longitudinal axis. The surgical instrument further includes a middle sleeve having a distal end, a proximal end, a passage therethrough, and a mid-longitudinal axis. The middle sleeve is sized and configured to be inserted into the passage of the outer sleeve. The surgical instrument further includes a trocar having a distal end, a proximal end, and a mid-longitudinal axis. The trocar is sized and configured to be inserted into the passage of the middle sleeve.

The method further includes placing the middle sleeve into the outer sleeve with at least a portion of the distal end of the middle sleeve extending beyond the distal end of the outer sleeve; placing the trocar into the middle sleeve with at least a portion of the distal end of the trocar extending beyond the distal end of the middle sleeve and the outer sleeve; inserting the surgical instrument with the distal end of the trocar into the bone; advancing into the bone the surgical instrument with the trocar, the middle sleeve, and the outer sleeve in fixed relationship to form an opening into the bone; removing the trocar from the middle sleeve with the middle sleeve and outer sleeve remaining in the bone; further advancing into the bone the surgical instrument with the middle sleeve and outer sleeve in fixed relationship to enlarge the opening being formed into the bone; removing the middle sleeve from the outer sleeve with the outer sleeve remaining in the bone; and further advancing into the bone the surgical instrument to enlarge the opening being formed into the bone.

It is to be understood that both the foregoing general description and the following detailed description are exemplary and explanatory only and are not restrictive of the invention, as claimed.

The accompanying drawings, which are incorporated in and constitute a part of the specification, illustrates several embodiments of the invention and together with the description, serve to explain the principles of the invention.

DETAILED DESCRIPTION OF THE PREFERRED EMBODIMENT

Reference will now be made in detail to the present preferred embodiments of the invention, examples of which are illustrated in the accompanying drawings.

FIGS. 1-7 illustrate a surgical instrument in accordance with one preferred embodiment of the present invention. Preferably, the surgical instrument includes several components that are each individually engageable to a handle configured to hold the components of the surgical instrument in fixed relationship and then remove the components of the surgical instrument either separately or in combinations of more than one component at a time. Where used herein, the term "component" may include, without limitation, an object that itself may be a stand-alone instrument.

Figure 1:
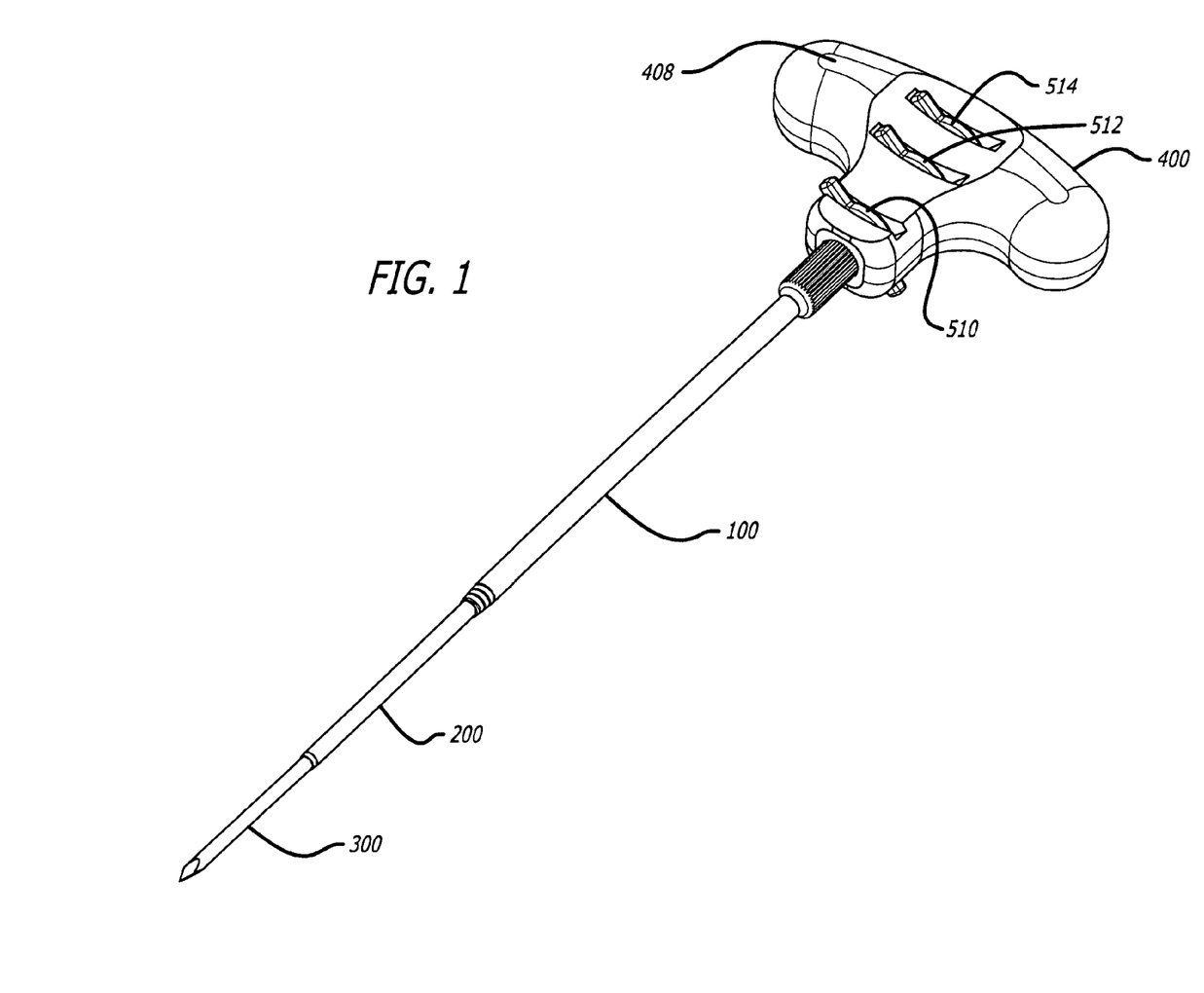
FIG. 1 is a perspective view of a surgical instrument in accordance with one preferred embodiment of the present invention.
Figure 2:
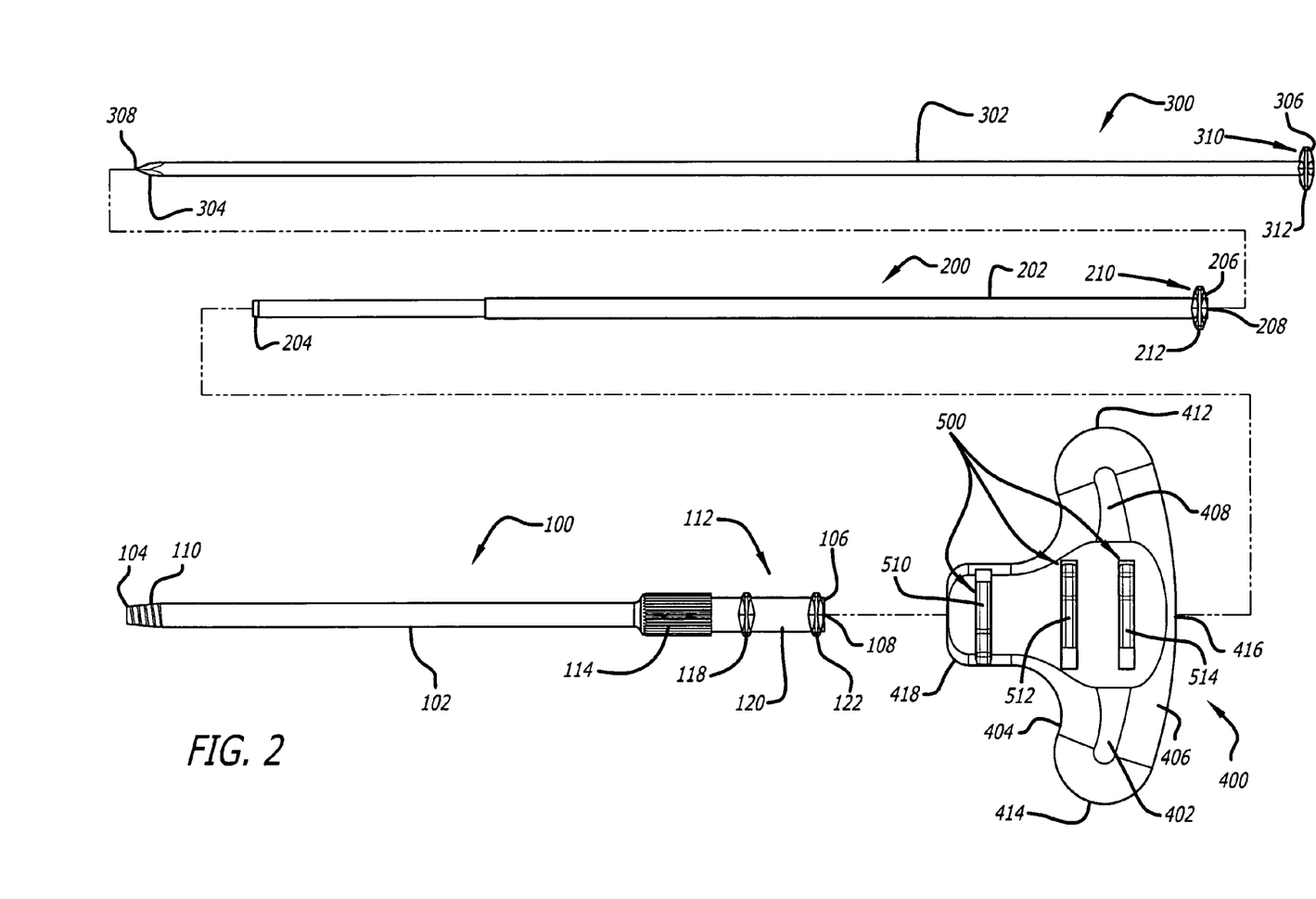
FIG. 2 is an exploded view of the surgical instrument of FIG. 1.

Referring to FIGS. 1 and 2, the surgical instrument includes an outer sleeve 100, a middle sleeve 200, a trocar 300, a handle 400, and a release mechanism 500 for releasably locking outer sleeve 100, middle sleeve 200, trocar 300, and handle 400 in a fixed relationship relative to one another. Upon engaging one or more portions of release mechanism 500, outer sleeve 100, middle sleeve 200, trocar 300, and handle 400 may be disengaged from one another, as will be described in further detail below.

As shown in FIG. 2, outer sleeve 100 includes a shaft 102, a distal end 104, a proximal end 106, and a passage 108 configured to receive a portion of middle sleeve 200 or other instrument therethrough. Passage 108 is in communication with distal end 104 and proximal end 106 and is hollow along shaft 102. Distal end 104 preferably includes a threaded portion 110. Portion 110 may also have a conical shape to facilitate entry of outer sleeve 100 into tissue. The thread of portion 110 engages outer sleeve 100 to bone. Proximal end 106 includes an enlarged portion 112 that serves as a base to secure outer sleeve 100 to handle 400.

Enlarged portion 112 preferably includes a grip portion 114 and a proximal portion 120. Grip portion 114 is configured for engagement with the fingers of a surgeon using the instrument. Proximal portion 120 preferably includes a first engagement projection 118 adapted to engage a portion of release mechanism 500. Proximal portion 120 further preferably includes a second engagement projection 122 which permits outer sleeve 100 to be locked at different lengths relative to handle 400, as will be described below. It will be appreciated that proximal portion 120 may, if desired, further include a thread that is adapted to cooperatively engage additional instruments, for example, a syringe or other type of medical instrument that is configured for use with a cannula or outer sleeve. Any one of the proximal ends of the outer sleeve, the middle sleeve, and the passage the handle may include a coupling such as a Luer connection adapted to convey a flowable material from a tube or a fluid-carrying vessel such as, but not limited to, a syringe, into one or more passages of the instrument.

Middle sleeve 200 includes a shaft 202, a distal end 204, a proximal end 206, and a passage 208 configured to receive a portion of trocar 300 or other instrument therethrough. Passage 208 is in communication with distal end 204 and proximal end 206 and is hollow along shaft 202. Proximal end 206 includes an enlarged portion 210 having an engagement projection 212 adapted to engage at least a portion of release mechanism 500. Alternatively, proximal end 206 of middle sleeve 200 may further include a release mechanism configured to lock directly to proximal end 106 of outer sleeve 100 such as, for example, having engagement projections for cooperatively engaging the outer sleeve. Enlarged portion 210 acts as a depth stop to limit insertion of middle sleeve 200 into outer sleeve 100. When enlarged portion 210 abuts proximal end 106 of outer sleeve 100, distal end 204 of middle sleeve 200 extends a predetermined distance beyond distal end 104 of outer sleeve 100 when middle sleeve 200 is engaged to outer sleeve 100.

Trocar 300 includes a shaft 302, a distal end 304, and a proximal end 306. Distal end 304 preferably includes a sharp tip 308. It will be appreciated by those of ordinary skill in the art that tip 308 may be of a variety of configurations without departing from the scope of the present invention. For example, tip 308 may include a single bevel, be multi-faceted, or have a conical shape as dictated by the needs of the surgical environment into which the trocar is intended to be used. Proximal end 306 of trocar 300 includes an enlarged portion 310 having an engagement projection 312 configured to engage at least a portion of release mechanism 500. Enlarged portion 310 is preferably sized and configured as a depth stop to limit the insertion of trocar 300 into middle sleeve 200. When engagement projection 312 is engaged with release mechanism 500, distal end 304 of trocar 300 extends a predetermined distance beyond distal end 204 of middle sleeve 200 when trocar 300 is engaged to middle sleeve 200. It will be appreciated that trocar 300 may include an enlarged portion or collar distally along the length from enlarged portion 310 to abut enlarged portion 210 of middle sleeve 200 and limit the insertion of trocar 300 into middle sleeve 200.

Shaft 302 of trocar 300 is preferably solid. As used herein, the term "trocar" refers to components or instruments that are solid or hollow broadly utilized to cut, separate or guide through tissue. Examples of such components or instruments include, but are not limited to, a wire, needle, stylet, and obdurator. It will be appreciated by those of ordinary skill in the art that shaft 302 may be hollow and have a passage therethrough to receive additional instruments or conduct materials therethrough without departing from the scope of the present invention.

Figure 3:
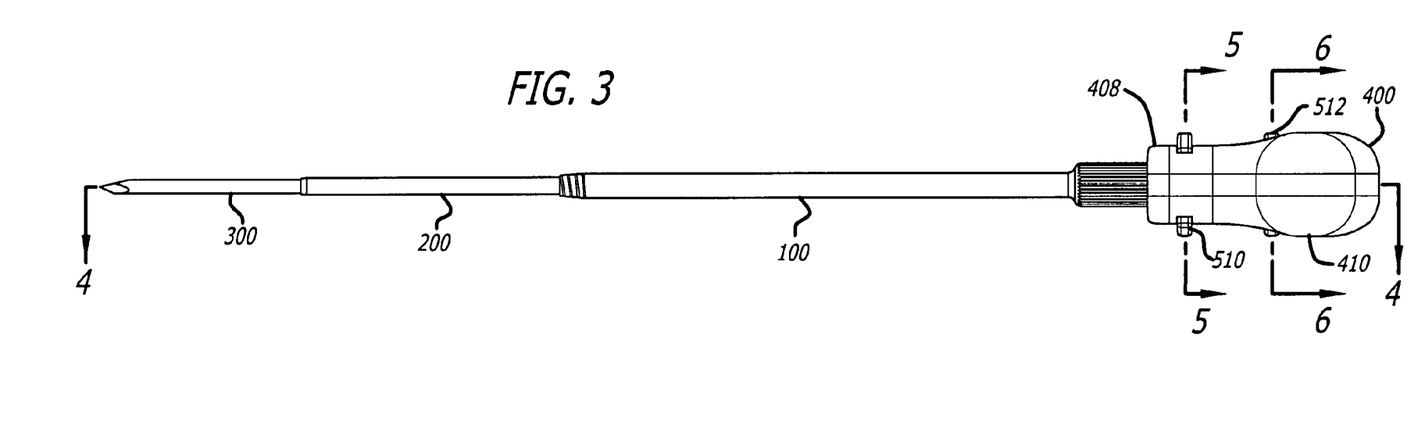
FIG. 3 is a side elevation view of the surgical instrument of FIG. 1.
Figure 4:
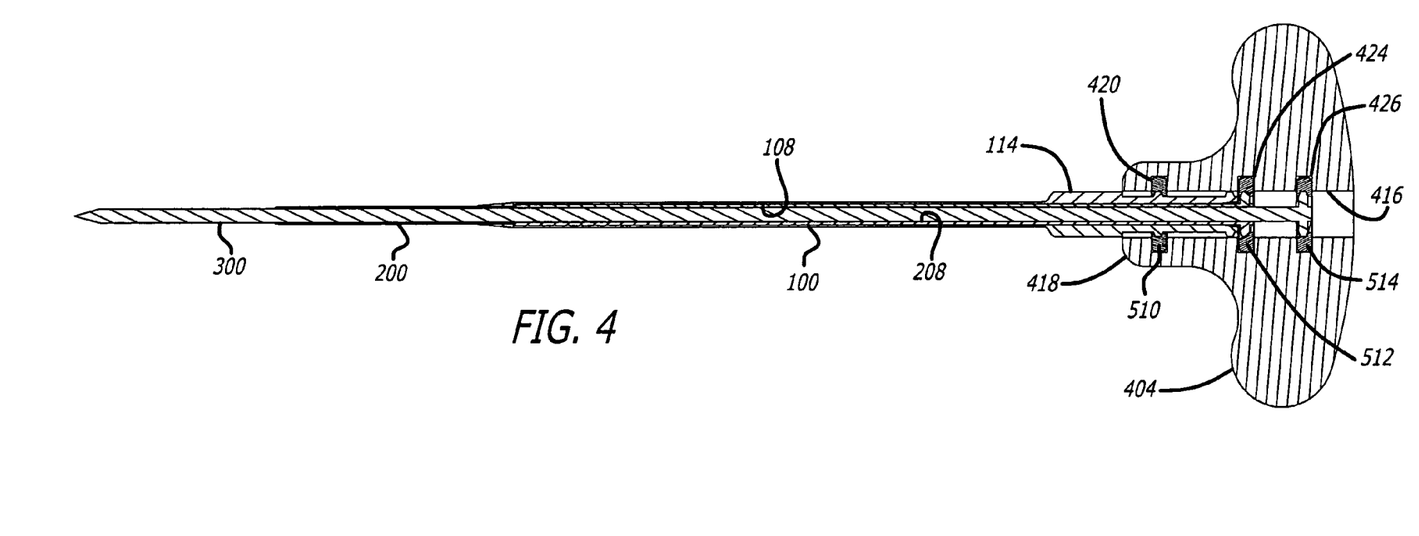
FIG. 4 is a cross-sectional side view of the surgical instrument of FIG. 1 taken along line 4-4 of FIG. 3.
Figure 5:
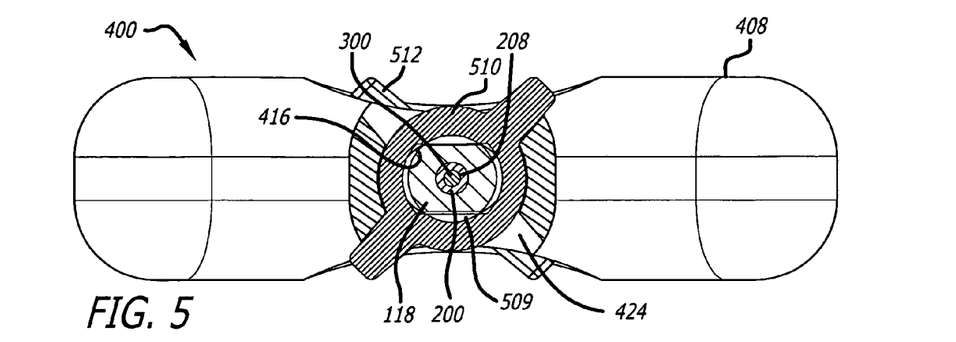
FIG. 5 is a transverse cross-sectional bottom view taken along line 5-5 of FIG. 3.
Figure 6A:
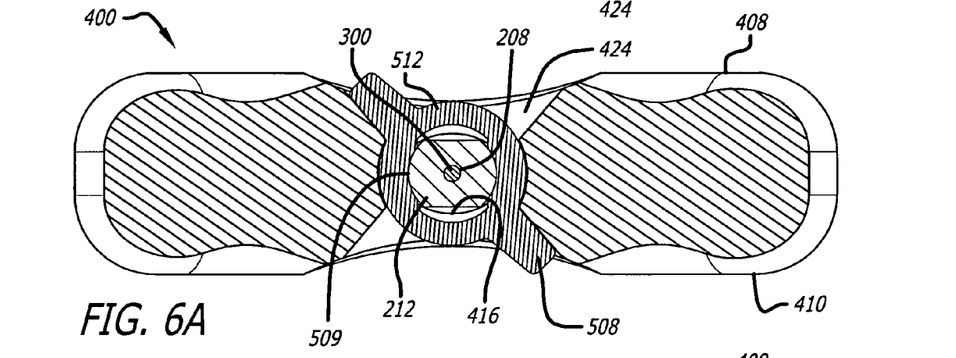
FIG. 6A is a transverse cross-sectional bottom view taken along line 6-6 of FIG. 3.
Figure 6B:
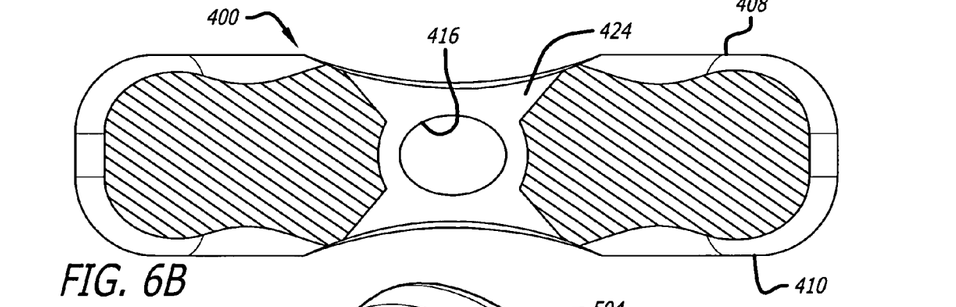
FIG. 6B is an alternative view of FIG. 6A without a portion of the release mechanism shown in cross section.

As shown in FIGS. 2-4, handle 400 includes a body 402 having a lower grip portion 404, a top surface 406, a front 408, a rear 410, sides 412, 414, and a passage 416 extending through lower grip portion 404 and top surface 406. As shown in FIGS. 5, 6A, and 6B, passage 416 preferably includes a cross section that is at least in part non-circular transverse to the mid-longitudinal axis of the instrument. When used with proximal portions of components inserted therein that have matching transverse cross sections that are at least in part non-circular, the handle may be used to more effectively impart rotational motion to the components attached to the handle. It will be appreciated that the passage having a non-circular transverse cross section is preferred only and that the passage may have a circular cross section without departing from the scope of the present invention.

Referring to FIGS. 2 and 4, lower grip portion 404 includes a stem 418 configured to be engaged by at least two fingers of the hand of a surgeon. Stem 418 further includes a first engagement recess 420 configured to engage at least a portion of release mechanism 500. Top surface 406 is preferably sized and configured to fit within the palm of a user's hand.

Handle 400 includes a second engagement recess 424 and a third engagement recess 426, each of which are preferably longitudinally space apart from one another along the length of the handle between lower grip portion 404 and top surface 406.

The proximal ends of outer sleeve 100, middle sleeve 200, and trocar 300 each preferably have an at least in part non-circular cross section transverse to the mid-longitudinal axis of the instrument, more preferably, a generally flattened oval-shaped cross section conforming to the cross sectional shape of passage 416 of handle 400. The at least in part non-circular transverse cross sectional shape facilitates rotating the components in unison. It will be appreciated that the non-circular transverse cross sectional shape is preferred only and that the components may have a circular transverse cross section without departing from the scope of the present invention.

Figure 7:
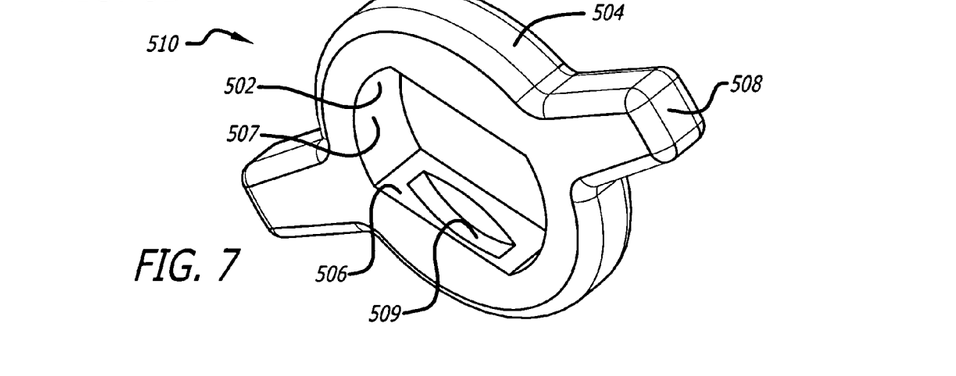
FIG. 7 is a perspective view of a release member in accordance with one preferred embodiment of the present invention.

Referring to FIGS. 1 and 7, release mechanism 500 includes a plurality of release members 510, 512, and 514. Release members 510, 512, and 514 are adapted to releasably lock outer sleeve 100, middle sleeve 200, and trocar 300, respectively, to handle 400. As shown in FIG. 7, release member 510 includes an interior surface 502 and an exterior surface 504. Interior surface 502 preferably includes parallel generally flat portions 506 and curved portions 507 for interaction with instruments inserted through the central through-opening of the release member. Exterior surface 504 preferably includes a plurality of finger-engaging projections 508 around the perimeter of release member 510. Release members 510, 512, and 514 are moveable by the surgeon from a first position to a second position to engage and disengage the components of the surgical instrument. It will be appreciated that other forms of finger-engaging projections may be utilized without departing from the scope of the present invention. For example, the finger engaging projections may be knurled, or may be omitted all together.

At least one of, but preferably both of the interior parallel flat portions 506 include a recess 509 adapted to receive a portion of an engagement projection of one of outer sleeve 100, middle sleeve 200, and trocar 300. Preferably, recess 509 has a slightly smaller dimension than the portion of the engagement projection it is adapted to engage so as to allow for a tight, interference fit between the release member and the engagement projection. Release members 510, 512, and 514 are preferably configured to be permanently fixed to handle 400 to prevent separation from handle 400.

As shown in FIGS. 2-6B, outer sleeve 100, middle sleeve 200, trocar 300, and handle 400 are preferably coaxially engageable with one another. To assemble the surgical instrument, middle sleeve 200 is inserted through the passage 108 of outer sleeve 100 until enlarged portion 210 is proximate proximal end 106 of outer sleeve 100. When assembled together, distal end 204 of middle sleeve 200 will preferably extend beyond distal end 104 of outer sleeve 100.

Next, trocar 300 is inserted into passage 208 of middle sleeve 200 until enlarged portion 310 is proximate enlarged portion 210 of outer sleeve 200. When engaged to middle sleeve 200, distal end 304 of trocar 300 will extend beyond distal end 204 of middle sleeve 200 and distal end 104 of outer sleeve 100 as shown in FIG. 3. If desired, enlarged portion 310 may be configured to act as a depth stop to limit the depth of penetration of trocar 300 into middle sleeve 200. Trocar 300 may be one of a set of trocars having different lengths, enabling the surgeon to select an appropriate trocar to achieve the surgical objective.

Handle 400 is engaged to outer sleeve 100, middle sleeve 200, and trocar 300 by sliding a portion of the proximal ends of outer sleeve 100, middle sleeve 200, and trocar 300 into passage 416 until the distal end of stem 418 abuts grip portion 114 of outer sleeve 100 as shown in FIG. 4.

After outer sleeve 100, middle sleeve 200, trocar 300, and handle 400 are all coaxially engaged to one another, they may be individually and releasably locked to one another by release mechanism 500. Outer sleeve 100 is locked to handle 400 by moving release member 510 from an unlocked, first position to a locked, second position within first engagement recess 420 of handle 400. As shown in FIG. 5, in the unlocked position, curved portions 507 (FIG. 7) are positioned around passage 416 of handle 400 so that the instruments may be slidably moved within passage 416 without interference from release member 510. Moving first release member 510 counter-clockwise about the mid-longitudinal axis of the instrument moves recess 509 to engage engagement projection 118 of outer sleeve 100.

FIG. 6A shows the locking of the middle sleeve to handle 400 with release member 512 being moved from the first position to the second position. Trocar 300 is locked to handle 400 with release member 514 in the same fashion as release member 510 and release member 512 are used to lock outer sleeve 100 and middle sleeve 200 to handle 400.

As shown in FIGS. 5 and 6A, each release member is preferably accessible from the front and back of handle 400 when locking an associated component to handle 400. Finger-engaging projections 508 are preferably off to one side of the engagement recess when the release member is in the locked or unlocked position. Such a configuration permits a surgeon to easily determine whether the associated component is locked or unlocked to handle 400 without having to visually observe the instrument.

Handle 400 may be used to individually engage or remove one or more of the components, singly or in combination. For example, handle 400 may be used to remove trocar 300 alone by moving release members 510 and 512 to the unlocked position and then moving handle 400 axially away from outer sleeve 100 and middle sleeve 200. Alternatively, handle 400 can be used to remove trocar 300 and middle sleeve 200 while leaving outer sleeve 100 in place by moving release member 510 to the unlocked position and then moving handle 400 axially way from outer sleeve 100. As a further alternative, handle 400 may be used to remove all three components at the same time by maintaining release members 510, 512, and 514 in their locked positions within their respective engagement recesses.

It will be appreciated that the order of engagement of outer sleeve 100, middle sleeve 200, trocar 300, and handle 400 may proceed in other ways. For example, outer sleeve 100 and handle 400 may be engaged to each other first, then outer sleeve 100 inserted into the upper end of passage 416 of handle 400, followed by trocar 300. Alternatively, middle sleeve 200 and trocar 300 may be engaged with each other, then inserted into outer sleeve 100. The combination of outer sleeve 100, middle sleeve 200, and trocar 300 may then be inserted into passage 416 from the lower end of the passage.

The length of outer sleeve 100 relative to handle 400 may be adjusted relative to handle 400 by aligning second engagement projection 122 with first engagement recess 420 and using release member 510 to lock outer sleeve 100 to handle 400. It will be appreciated that middle sleeve 200 and/or trocar 300 may also include multiple engagement projections to permit for adjustably locked lengths relative to handle 400.

Referring now to FIGS. 8-13, a method for sequential dilation of tissue will now be described in relation to a surgical procedure in the spine in association with the surgical instrument set forth above. It will be appreciated that the surgical instrument and method of the present invention may be used in other areas of the human body for other purposes other than sequential dilation. For example, the surgical instrument may be used for delivering a therapeutic material to soft tissue, providing an access into the body for an imaging device such as an endoscopic camera, or as a conduit for irrigation and/or suction.

Figure 8:
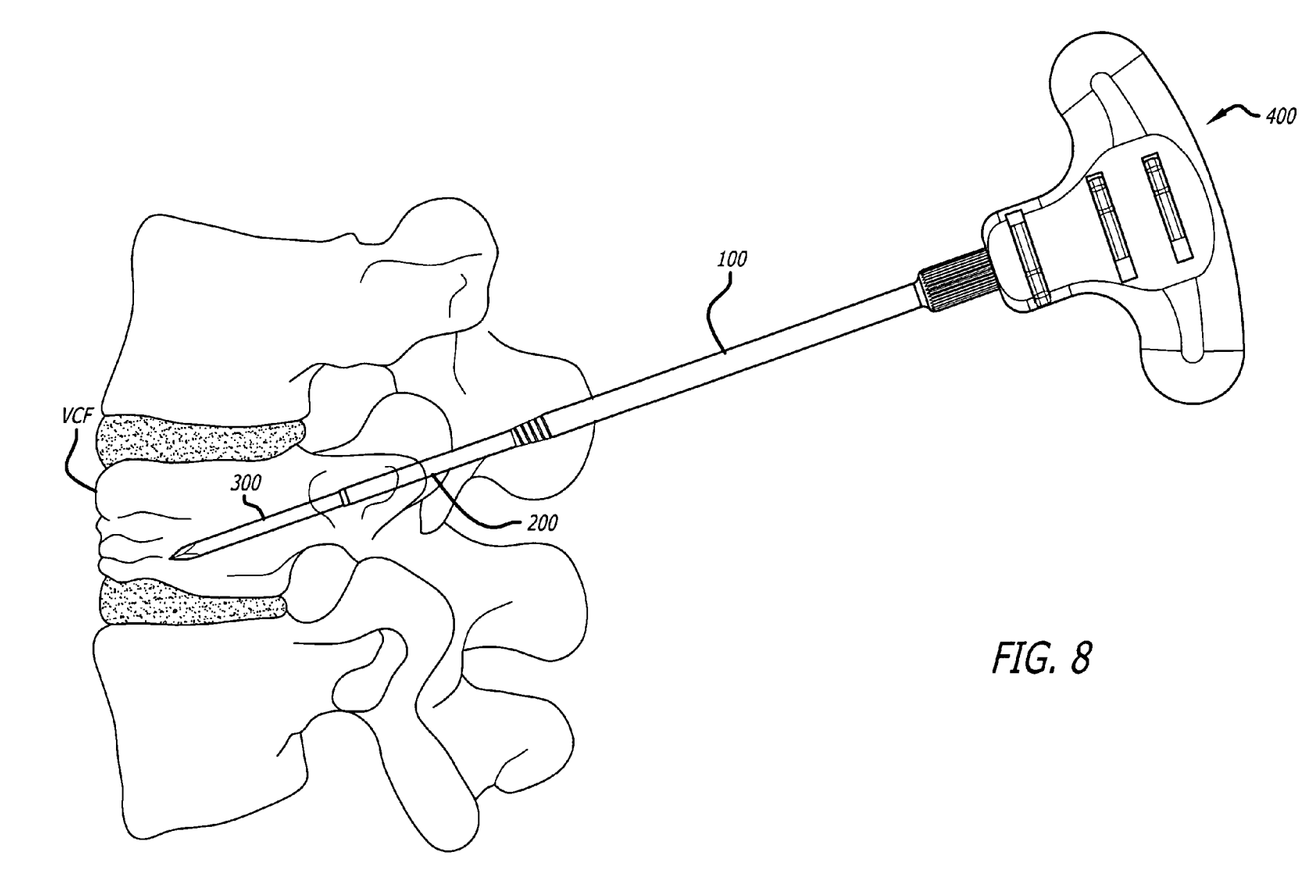
FIG. 8 is a side elevation view of the surgical instrument of FIG. 1 being inserted into a vertebra of the human spine.
Figure 9:
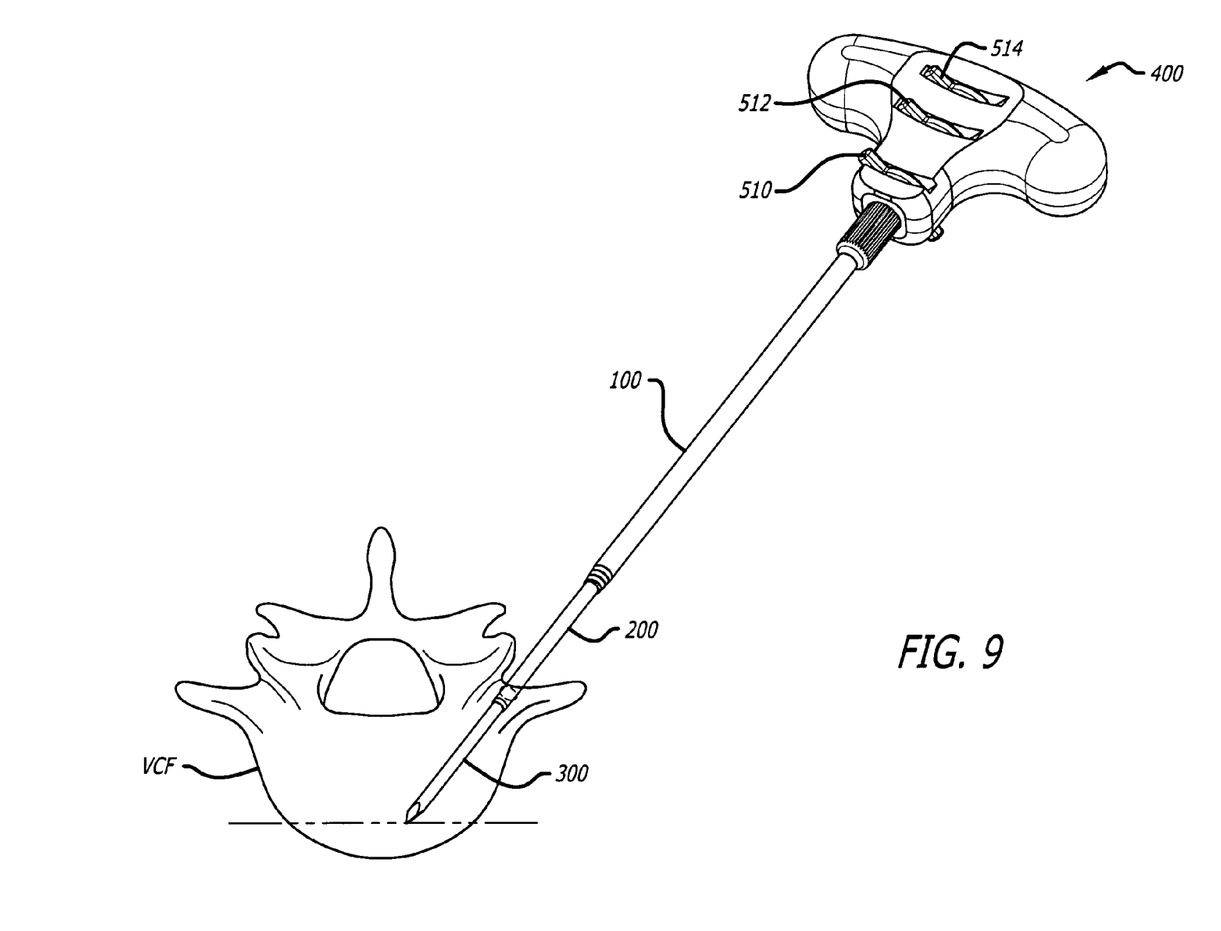
FIG. 9 is a partial cross-sectional top view of a vertebra of the human spine with the surgical instrument of FIG. 1 being advanced until a trocar of the surgical instrument reaches a predetermined depth in the vertebra.
Figure 10:
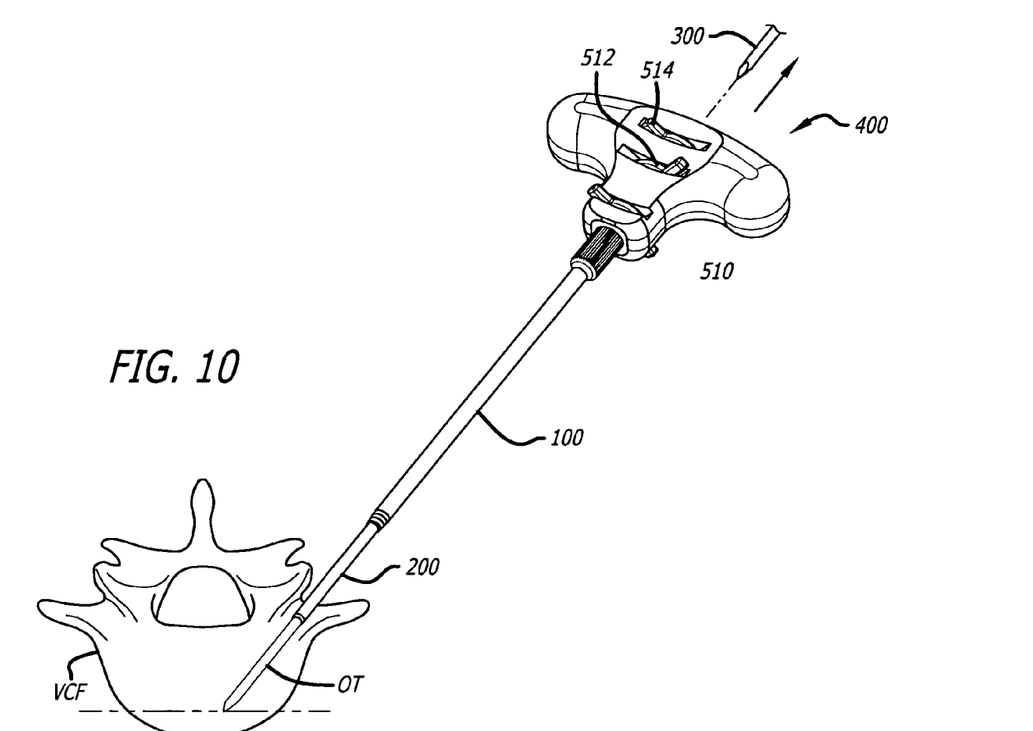
FIG. 10 is a partial cross-sectional top view of the vertebra with the trocar being removed from a middle sleeve and outer sleeve of the surgical instrument and illustrating the opening formed by the trocar.

As shown in FIG. 8, after being fully assembled together, the surgical instrument is inserted through the pedicle of the vertebra and into the vertebral body so that the distal end of trocar 300 penetrates the interior of the vertebral body. The procedure is preferably done under fluoroscopy so that the surgeon may visualize placement of the instrument relative to the bone tissue. Preferably, the distal end of the trocar is advanced until it reaches a predetermined location, such as the first third of the anterior portion of the vertebral body being operated upon. It is preferred that the predetermined location is a sufficient distance from the anterior wall of the vertebral body to prevent over penetration of the vertebral body. Penetration through the anterior wall could result in damage to the neurological and vascular structures adjacent the anterior aspect of the vertebral body. A breach of the anterior wall could permit any materials being inserted through the surgical instrument to flow out of the vertebral body and cause damage to the surrounding structures. Once the surgical instrument has been advanced to the predetermined depth in the vertebral body, trocar 300 is removed from middle sleeve 200 and outer sleeve 100 with middle sleeve 200 remaining in the bone as shown in FIG. 10. The withdrawal of trocar 300 leaves an opening OT formed by trocar 300.

Figure 11:
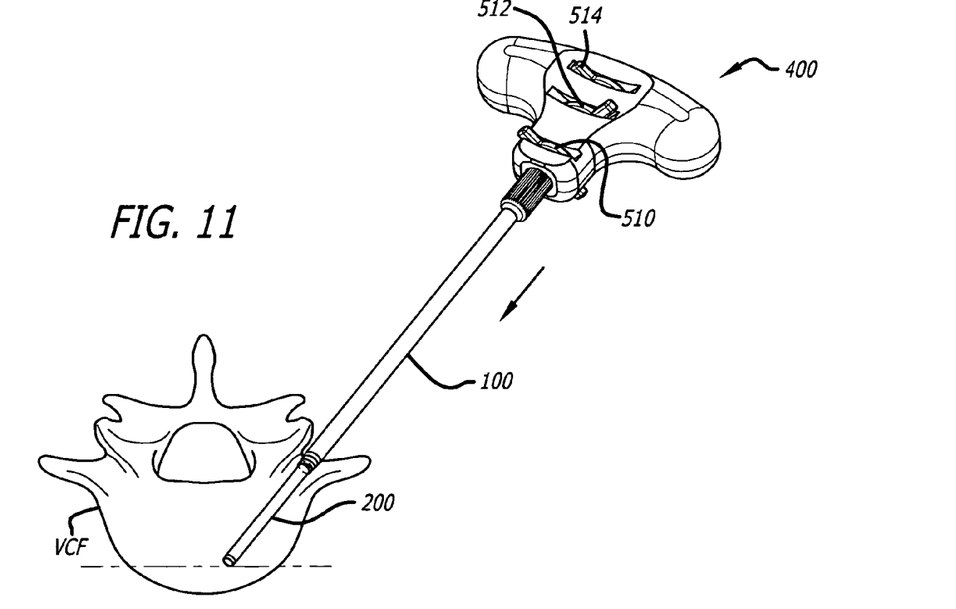
FIG. 11 is a partial cross-sectional top view of the vertebra with the middle and outer sleeves being advanced until the middle sleeve reaches the predetermined depth in the vertebra to enlarge the opening formed by the trocar.
Figure 12:
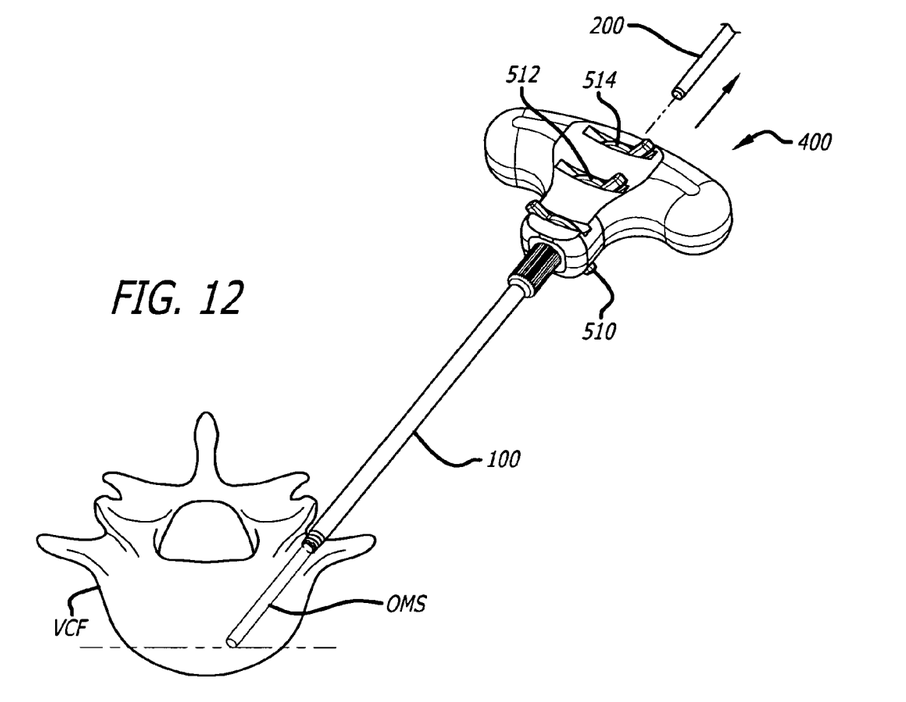
FIG. 12 is a partial cross-sectional top view of the vertebra with the middle sleeve being removed from the outer sleeve and illustrating the enlarged opening formed by the middle sleeve.

Next, the surgeon advances into the bone middle sleeve 200 of the surgical instrument until the distal end of middle sleeve 200 reaches the predetermined depth to enlarge opening OT as shown in FIG. 11. When the distal end of middle sleeve 200 has been inserted to the predetermined location or depth within the vertebral body, middle sleeve 200 is removed from outer sleeve 100 with outer sleeve 100 remaining in the bone as shown in FIG. 12. The withdrawal of middle sleeve 200 leaves an opening OMS formed in the bone by middle sleeve 200 that has a transverse dimension larger than the transverse dimension of the opening formed by trocar 300.

Figure 13:
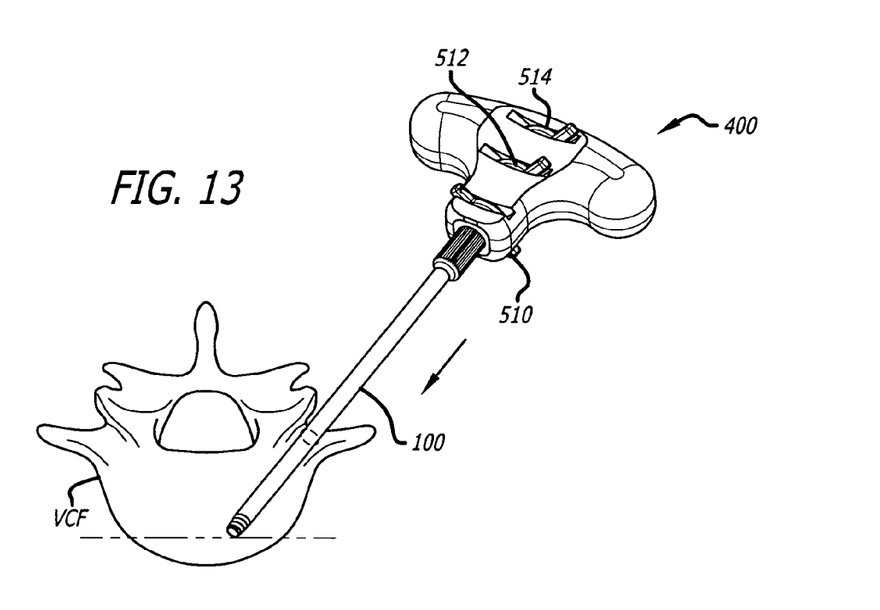
FIG. 13 is a partial cross-sectional top view of the vertebra with the outer sleeve being advanced until the outer sleeve reaches the predetermined depth in the vertebra to enlarge the opening formed by the middle sleeve.

The surgeon then advances outer sleeve 100 into the bone until the distal end of outer sleeve 100 reaches the predetermined depth to enlarge opening OMS as shown in FIG. 13. When outer sleeve 100 is advanced nearly to the predetermined depth, the surgeon may rotate outer sleeve 100 to engage thread 110 with the surrounding bone to fixedly locate outer sleeve within the surgical site. After enlarging the opening, outer sleeve 100 may be withdrawn or may remain in position for subsequent use in combination with other instruments such as a bone removal device, or to deliver a therapeutic material to the site.

It will be appreciated by those of ordinary skill in the art that the steps of the method set forth above may be varied without departing from the scope of the present invention. The method set forth above may omit steps or include additional steps. For example, a second middle sleeve may be placed into the outer sleeve so that a portion of the distal end of the second middle sleeve may extend beyond the distal end of the outer sleeve. Once trocar 300 and middle sleeve 200 have been removed, the surgeon may engage another instrument to outer sleeve 100 for additional procedures.

With outer sleeve 100 remaining in the vertebra, the surgeon may introduce a material through outer sleeve 100 and into the surgical site. Examples of materials useable with the surgical instrument include bone morphogenetic protein, hydroxyapatite, hydroxyapatite tricalcium phosphate, an antimicrobial substance, or bone cement. It will be appreciated that other substances and materials may be introduced through outer sleeve 100 without departing from the scope of the present invention.

The surgeon may fix outer sleeve 100 to the bone by engaging thread 110 at the entrance to the opening formed by trocar 300 and/or middle sleeve 200. If desired, the surgeon may fix outer sleeve 100 to the pedicle of the vertebra by engaging thread 110 into the pedicle. The tapered profile of thread 110 permits the surgeon the option to either push outer sleeve 100 into the opening, and then engage thread 110 to the bone, or to immediately engage thread 110 into the bone.

The components of the surgical instrument are made of a surgical grade material. Examples of suitable materials include, but are not limited to, metal such as stainless steel, titanium, and nitinol, carbon composites, and one or more plastic polymers. It will be appreciated that the components of the surgical instrument may be made of any combination of metal, plastic, carbon composite, or other materials suitable for the intended purpose.

In a preferred embodiment of the present invention, outer sleeve 100 preferably has a maximum length along the mid-longitudinal axis of the surgical instrument that is approximately 10 to 15 cm between distal end 104 and proximal end 106. Passage 108 of outer sleeve 100 preferably has a minimum transverse cross-sectional dimension approximately in the range of 4 to 6 mm and a maximum transverse cross-section dimension approximately in the range of 3 to 20 mm. It will be appreciated that the dimensions set forth above may be varied without departing from the scope of the present invention.

Middle sleeve 200 preferably has a maximum length in the range of approximately 15 to 21 cm along the mid-longitudinal axis of the surgical instrument. Passage 208 of middle sleeve 200 preferably has a minimum transverse cross-sectional dimension in the range of at least 2 to 4 mm and a maximum transverse cross-sectional dimension in the range of approximately 2.5 to 15 mm. It will be appreciated that the dimensions set forth above may be varied without departing from the scope of the present invention.

Trocar 300 preferably has a maximum length along a mid-longitudinal axis of the surgical instrument in the range of approximately 21 to 26 cm along the mid-longitudinal axis of the surgical instrument. Shaft 302 of trocar 300 preferably has a minimum transverse cross-sectional dimension along the mid-longitudinal axis of the surgical instrument at least in the range of 0.5 to 2.5 mm. It will be appreciated that the dimensions set forth above may be varied without departing from the scope of the present invention.

When outer sleeve 100, middle sleeve 200, and trocar 300 are assembled together, shaft 302 will preferably extend 2 to 4 cm beyond the distal end of middle sleeve 200. Shaft 202 of middle sleeve 200 will preferably extend 2 to 4 cm beyond the distal end of outer sleeve 100. The length of shaft 102 of outer sleeve 100 is preferably in the range of one-fourth to three-quarters the length of shaft 302 of trocar 300, more preferably in the range of one-third to one-half the length of shaft 302.

Release members 510, 512, and 514 each preferably have a maximum cross-sectional dimension transverse to the mid-longitudinal axis of the surgical instrument when engaged thereto that is greater than the minimum dimension of handle 400 between front 408 and rear 410 of handle 400.

The shafts of outer sleeve 100, middle sleeve 200, and trocar 300 each preferably have a generally circular cross-sectional shape transverse to the mid-longitudinal axis of the surgical instrument. It will be appreciated by those of ordinary skill in the art that the cross-sectional shape of any one or all of the components may be varied without departing from the scope of the present invention. For example, the cross section of any one or all of the components may be square, rectangular, oval, or any other cross section suitable for the intended purpose. Additionally, one or more of the components may have an overall shape that is generally cylindrical, conical, or cylindrical with a conical distal end.

The ends of outer sleeve 100 and middle sleeve 200 are preferably open. The openings of each end may be of the same or different transverse size relative to the mid-longitudinal axis of the instrument. The passages of outer sleeve 100 and middle sleeve 200 are preferably configured to conduct a flowable material into a patient.

There are numerous advantages of the present invention. For example, a single handle may be used to engage and disengage one or a plurality of components. This has the advantage of permitting the surgeon to concentrate on the surgical procedure rather than worrying about which handle to grasp to engage or disengage a particular instrument. The placement of the release mechanism permits easy access so that the surgeon can quickly discern the release member associated with a particular component and release the component by moving the thumb or forefinger of the surgeon's hand. The configuration of the handle is adapted if so desired to have multiple components within a single instrument, which reduces error due to repositioning of multiple instruments. The dilating ability of the surgical instrument allows for easier placement of the instrument within tissue.

It will be appreciated by those of ordinary skill in the art that the present invention described above may take alternative forms without departing from the scope of the present invention. For example, the surgical instrument may include more than or less than three components. Each component may have more than one passage or lumen. The proximal end of each component may have a depth stop that is adjustable along the length of the respective component. Instead of a release member, a spring-lock mechanism may be used to releasably engage and disengage the components to one another. The release members may also have an incomplete perimeter having a general C-shape. Handle 400 may be a shape other than a generally T-shaped configuration. For example, handle 400 may have a grip portion that is generally parallel to the mid-longitudinal axis of the surgical instrument.

The release mechanism of the present invention is applicable to a wide variety of components for surgical instruments. For example and without limitation, the outer component of the surgical instrument could be a sheath, sleeve, retractor, or any other tubular or cannulated member. The middle component of the surgical instrument could be a middle sleeve, a drill sleeve, or any other tubular or cannulated member. The inner component of the surgical instrument could be a stylet, obdurator, trocar, needle, bone tamp, forceps, surgical irrigation device, endoscopic imaging equipment, or any other instrument insertable into a tubular member having a portion adapted to extend beyond the distal end of the tubular member.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for forming an opening in bone comprising: providing a surgical instrument comprising:
    an outer sleeve having a distal end, a proximal end, a passage therethrough, and a mid-longitudinal axis;
    a middle sleeve having a distal end, a proximal end, a passage therethrough, and a mid-longitudinal axis, the middle sleeve being sized and configured to be inserted into the passage of the outer sleeve;
    a trocar having a distal end, a proximal end, and a mid-longitudinal axis, the trocar being sized and configured to be inserted into the passage of the middle sleeve;
placing the middle sleeve into the outer sleeve with at least a portion of the distal end of the middle sleeve extending beyond the distal end of the outer sleeve;
placing the trocar into the middle sleeve with at least a portion of the distal end of the trocar extending beyond the distal end of the middle sleeve and the outer sleeve;
inserting the surgical instrument with the trocar, the middle sleeve, and the outer sleeve in fixed relationship to insert the distal end of the trocar into the bone;
advancing into the bone the surgical instrument with the trocar, the middle sleeve, and the outer sleeve in fixed relationship to a predetermined depth in the bone to form an opening into the bone;
removing the trocar from the middle sleeve with the middle sleeve and outer sleeve in fixed relationship remaining in the bone;
further advancing into the bone the surgical instrument with the middle sleeve and outer sleeve in fixed relationship to enlarge the opening being formed into the bone, the middle sleeve being inserted into the bone to approximately the same predetermined depth of the trocar;
removing the middle sleeve from the outer sleeve with the outer sleeve remaining in the bone; and
further advancing into the bone the surgical instrument to enlarge the opening being formed into the bone, the outer sleeve being inserted into the bone to approximately the same predetermined depth of the trocar.

2. The method of claim 1, wherein the bone is a vertebra.

3. The method of claim 1, further comprising rotating the entire instrument at least in part during insertion.

4. The method of claim 1, further comprising threadably engaging the distal end of the outer sleeve into the bone.

5. The method of claim 1, wherein the further advancing into the bone the surgical instrument further includes advancing the instrument through a pedicle of a vertebra.

6. The method of claim 1, wherein the predetermined depth is the anterior third of a vertebral body.

7. The method of claim 1, further comprising placing a second middle sleeve into the outer sleeve with at least a portion of the distal end of the second middle sleeve extending beyond the distal end of the outer sleeve.

8. The method of claim 1, further comprising introducing another instrument through the outer sleeve and into the opening formed into bone.

9. The method of claim 1, further comprising introducing a material through the outer sleeve and into the opening formed into the bone.

10. The method of claim 1, further comprising providing a handle having a passage coaxial with the passage of the outer sleeve, the passage of the middle sleeve, and the mid-longitudinal axis of the trocar, the handle being adapted to be removably coupled to the outer sleeve.

11. The method of claim 10, wherein the removing the trocar includes using the handle to withdraw only the trocar from the bone.

12. The method of claim 10, wherein the removing the middle sleeve includes using the handle to withdraw only the middle sleeve from the bone.

13. The method of claim 10, wherein the handle includes a release mechanism and further comprising placing the release mechanism in a first position for holding the trocar, the middle sleeve, and the outer sleeve in fixed relationship to the handle.

14. The method of claim 13, further comprising placing the release mechanism in a second position for holding the middle sleeve and the outer sleeve in fixed relationship to the handle.

15. The method of claim 14, further comprising placing the release mechanism in a third position for holding the outer sleeve in fixed relationship to the handle.

16. The method of claim 10, further comprising withdrawing at least one of the middle sleeve and the trocar through the passage of the handle.

17. The method of claim 13, further comprising rotating the release mechanism.

* * * * *

UNITED STATES PATENT AND TRADEMARK OFFICE
CERTIFICATE OF CORRECTION

| | | |
|---|---|---|
| PATENT NO. | : 7,842,038 B2 | Page 1 of 1 |
| APPLICATION NO. | : 11/417633 | |
| DATED | : November 30, 2010 | |
| INVENTOR(S) | : Sean M. Haddock et al. | |

It is certified that error appears in the above-identified patent and that said Letters Patent is hereby corrected as shown below:

<u>Title Page 1, Column 2:</u>
Line 12: change "Ahlstroem" to -- Akerfeldt --.

Signed and Sealed this
Eighth Day of February, 2011

David J. Kappos
*Director of the United States Patent and Trademark Office*